(12) United States Patent
Looper et al.

(10) Patent No.: US 12,004,770 B2
(45) Date of Patent: *Jun. 11, 2024

(54) CATHETER DESIGN FOR USE IN TREATING PLEURAL DISEASES

(71) Applicant: CAREFUSION 2200, INC., San Diego, CA (US)

(72) Inventors: Anthony Looper, Lake Zurich, IL (US); John A. Krueger, Muskego, WI (US); Jeffrey Schmitt, Trumbull, CT (US)

(73) Assignee: CAREFUSION 2200, INC., San Diego, CA (US)

( * ) Notice: Subject to any disclaimer, the term of this patent is extended or adjusted under 35 U.S.C. 154(b) by 713 days.

This patent is subject to a terminal disclaimer.

(21) Appl. No.: 17/068,593

(22) Filed: Oct. 12, 2020

(65) Prior Publication Data
US 2021/0022761 A1 Jan. 28, 2021

Related U.S. Application Data

(63) Continuation of application No. 13/696,555, filed as application No. PCT/US2011/035545 on May 6, 2011, now Pat. No. 10,799,263.

(60) Provisional application No. 61/332,547, filed on May 7, 2010.

(51) Int. Cl.
*A61B 17/3207* (2006.01)
*A61M 16/04* (2006.01)
*A61M 25/00* (2006.01)

(52) U.S. Cl.
CPC ..... *A61B 17/3207* (2013.01); *A61M 16/0406* (2014.02); *A61M 25/0068* (2013.01); *A61M 2025/006* (2013.01); *A61M 2025/0096* (2013.01); *A61M 2210/101* (2013.01)

(58) Field of Classification Search
CPC .......... A61B 17/3207; A61M 16/0406; A61M 25/0068; A61M 2025/006; A61M 2025/0096; A61M 2210/101
See application file for complete search history.

(56) References Cited

U.S. PATENT DOCUMENTS

2008/0221566 A1* 9/2008 Krishnan ............... A61B 34/20 606/41
2009/0205643 A1* 8/2009 Tanaka .................. A61M 25/10 128/200.24

* cited by examiner

*Primary Examiner* — Ashley L Fishback
*Assistant Examiner* — Chima U Igboko
(74) *Attorney, Agent, or Firm* — ArentFox Schiff LLP

(57) ABSTRACT

A catheter for use in treating pleural diseases, such as pleural effusions and pneumothorax, includes a tip portion that is configured to irritate the pleura when the catheter is inserted in the pleural cavity, thereby initiating mechanical pleurodesis. The tip portion has a substantially rough configuration and may include one or more protrusions that contact the pleura when the catheter is in use, thereby irritating the layers. This irritation causes the creation of fibrous adhesions between the parietal and visceral layers that close off the pleural cavity and prevent further fluid and/or air accumulations that occur as a result of pleural diseases.

21 Claims, 5 Drawing Sheets

CATHETER DESIGN FOR USE IN TREATING PLEURAL DISEASES

CROSS-REFERENCE TO RELATED APPLICATIONS

This Application is a Continuation of U.S. application Ser. No. 13/696,555 filed Apr. 29, 2013, which is a 371 National Stage of PCT/US2011/035545 filed May 6, 2011, which claims the benefit of U.S. Provisional Application No. 61/332,547 filed May 7, 2010, the entirety of which are incorporated by reference herewith.

FIELD OF THE INVENTION

The present invention relates to an improved catheter design for use in treating pleural diseases.

BACKGROUND OF THE INVENTION

The pleural cavity and the pleura serve an important function of aiding in the optimal functioning of the lungs during respiration. Diseases affecting the pleural cavity and pleura include pleural effusions and pneumothorax. Pleural effusions involve the build-up of fluid around the lungs. Pleural effusions can be associated with conditions such as cancer, tuberculosis, congestive heart failure, pneumonia, pulmonary emboli, viral disease, cirrhosis, post coronary artery bypass graft surgery, gastrointestinal disease, tuberculosis, and mesothelioma. Pneumothorax occurs when air or gas is present in the pleural cavity.

Patients with pleural diseases such as symptomatic pleural effusions or pneumothorax are typically treated with thoracentesis to remove fluid or air, and/or chemical or mechanical pleurodesis. Pleurodesis involves irritation of the parietal and/or visceral layers of the pleura to close off the pleural cavity and prevent further fluid and/or air accumulations. Pleurodesis is typically characterized by the creation of fibrous adhesions between the parietal and visceral layers of the pleura.

Mechanical pleurodesis can be achieved, for example, with the insertion of a rough pad or a catheter into the pleural cavity. Catheters are used in many medical procedures and are typically inserted into a patient's body cavity, duct, or vessel. Catheters are typically used to drain fluids, inject fluids, and to provide access for surgical instruments into or from a body cavity. Catheters may allow a user, such as a doctor, nurse, or other medical professional, to access a specific portion of a patient's body without making invasive incisions.

When using a catheter to perform mechanical pleurodesis, the tip of the catheter may be used to irritate the parietal and/or visceral layers of the pleura, thereby causing the creation of fibrous adhesions between the parietal and visceral layers. Typical catheters, however, are not highly effective in adequately irritating the parietal and visceral layers because they are substantially smooth.

Thus, there is a need in the art for an improved catheter design for use in treating pleural diseases.

SUMMARY OF THE INVENTION

The present invention provides a catheter for use in treating pleural diseases, such as pleural effusions and pneumothorax. The catheter may be inserted within the pleural cavity of a patient's lungs for initiating mechanical pleurodesis. The catheter includes a tip portion that is configured to irritate the pleura when the catheter is inserted in the pleural cavity. This irritation causes the creation of fibrous adhesions between the parietal and visceral layers that close off the pleural cavity and prevent further fluid and/or air accumulations that occur as a result of pleural diseases.

Other novel features and advantages of the present invention will become apparent to those skilled in the art upon examination of the following or upon learning by practice of the invention.

DETAILED DESCRIPTION OF THE INVENTION

Figure 1:
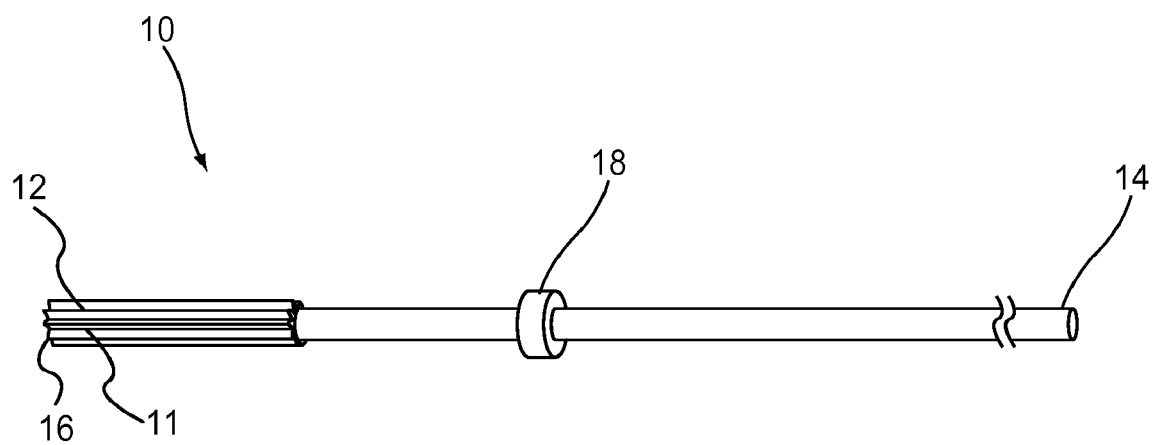
FIG. 1 shows a catheter according to an embodiment of the invention.

The present invention provides a catheter for use in treating pleural diseases, such as pleural effusions and pneumothorax. The catheter may be inserted within the pleural cavity of a patient's lungs for initiating mechanical pleurodesis. The catheter includes a tip portion that is positioned toward its distal end that is configured to irritate the pleura when the catheter is inserted in the pleural cavity. This irritation causes the creation of fibrous adhesions between the parietal and visceral layers that close off the pleural cavity and prevent further fluid and/or air accumulations that occur as a result of pleural diseases.

The surface of the tip portion has a substantially rough configuration that is capable of irritating the pleura when the catheter is inserted in the pleural cavity. The tip portion's surface may include one or more protrusions that contact the pleura when the catheter is in use, thereby irritating the layers.

The roughness of the tip portion may be varied to achieve a desired degree of irritation of the pleura based on a patient's condition. In general, a catheter tip portion having a roughness of about 50 to about 600 microinches, measured according to the ANSI B46.1-2002 Surface Texture Standard is desirable to initiate pleurodesis.

The shape, size, and arrangement of the protrusions may be varied to achieve a catheter tip surface with the desired roughness. The protrusions may be of any shape, size, and arrangement that can effectively irritate the pleura to initiate pleurodesis. For example, the cross-section of a protrusion may be polygonal, such as triangular, rectangular, or other polygonal. Alternatively, the cross-section of a protrusion may be substantially curved, such as circular, semi-circular or elliptical. In addition, any combination of cross-sections of protrusions may be used in a single catheter.

The size of the protrusions may be varied depending on the degree of irritation of the pleura desired. Typically, larger protrusions result in a higher degree of irritation in the pleura than do smaller protrusions. The protrusions typically range in size from about 50 to about 600 microinches in height measured on the surface of the catheter portion that is inserted in the pleural space. The protrusions are generally positioned near the tip portion of the catheter from about ½ to about 15 inches from the distal (inserted) end of the catheter. They may also be located at a portion of the catheter other than the tip portion, but still along a surface of the inserted portion of the catheter.

The protrusions formed near or at the tip portion of the catheter according to the present invention may be substantially uniform or irregular in size and shape. For example, the size and shape of the protrusions may be varied along the length of the tip portion of the catheter to better irritate the pleura. Larger protrusions may be present at the proximal end of the catheter, while smaller ridges may be present towards the distal end of the catheter, thereby forming a cone-shaped tip portion.

The protrusions may be arranged near or at the tip portion of the catheter in any orientation that allows the catheter to effectively irritate the pleura. In particular, the protrusions may be oriented randomly or oriented to form one or more continuous or discontinuous patterns on the surface of the catheter. For example, the protrusions may form ridges that may be substantially linear or curved. When the protrusions form a discontinuous ridge, the protrusions may appear as teeth at the tip portion of the catheter. If the catheter is oval in cross-section, the protrusions may be located on the elongated portion of the oval, and not along the curved portion of the oval, or vice versa, or on both the elongated and curved portions of the oval.

The protrusions may be oriented closely together, or there may be some space between the protrusions. Further, the density of protrusions on a tip portion's surface may be varied in a single catheter. For example, a higher density of protrusions may be present towards the distal end of the inserted portion of the catheter while a lower density of protrusions may be present towards the proximal end of the inserted portion.

The protrusions near or at the tip portion of the catheter may be formed of any material that is known in the art that is able to irritate the pleura. The material preferably has sufficient rigidity so that the protrusions are able to irritate the pleural layers. These materials may include, but are not limited to, silicone, PVC, polypropylene, polyurethane, other thermoplastic elastomers, etc.

The protrusions may be formed by any method known in the art including, but not limited to, molding, extrusion, coextrusion, overmolding, machining, etching, EDM, sputtering, vapor deposition, etc. They may also be formed by various material removal or deposition techniques. The protrusions may be formed separately from and then attached to the tip portion of the catheter, or they may be formed integrally with the tip portion of the catheter.

The catheter of the invention may be used to initiate pleurodesis by inserting the distal end of the catheter into the pleural cavity and contacting the protrusions at or near the distal tip portion of the catheter with the pleura. This contact between the protrusions and the pleura irritates the pleura, thus initiating pleurodesis. The contact may be achieved by the natural movement of the catheter positioned in the pleural space, or by a more active method such as by an external movement, agitation, or force such as a wire that is inserted through the catheter, a magnet that acts on the catheter, etc.

Any shape, size, or style of catheter that is known in the art may be used in the present invention. The catheter typically has a circular cross-section, but it may be of any other shape including, but not limited to, oval, elliptical, triangular, rectangular, or other polygonal. The catheter may be flexible or rigid and may be made of any material that is known in the art. For example, the catheter may be made of a polymer, such as silicone, that is inert and unreactive to body fluids and a range of medical fluids with which it may come into contact, or other materials that are known to have at least a mildly irritating effect on human tissues or cells.

The catheter of the invention may optionally include fenestrations, which allow fluid from a patient's body cavity to pass through them, thereby removing the fluid from the cavity towards a center lumen. The size of the fenestrations may vary, but they are typically of a size sufficient to allow bodily fluids to pass through them without clogging. The fenestrations may be arranged randomly or in a specified pattern.

The catheter may also include a cuff that assists in positioning the catheter in a patient's body cavity and in surrounding tissues and may reduce the occurrence of infection by creating a seal that prevents external microorganisms from penetrating and infecting the pleural space. The cuff may be made of any suitable material that is commonly used in catheters including, but not limited to, polyester.

An example of a catheter according to an embodiment of the invention is shown in FIG. 1. The catheter 10 includes a distal end 12 and a proximal end 14. A tip portion 16 is positioned towards or at the distal end 12 and includes protrusions 11. The proximal end 14 may be joined to a drainage container or other medical device. The catheter 10 may include a cuff 18.

According to an embodiment of the invention, a catheter of any cross-section includes a tip portion towards or at its distal end that has one or more protrusions of any size or shape. The protrusions may be positioned on a surface of the tip portion of the catheter.

Figure 2A:
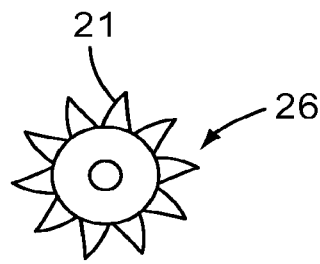
FIG. 2a is a cross-sectional view of a tip portion of a catheter according to an embodiment of the invention.

An example of a tip portion with protrusions according to this embodiment is shown in FIG. 2a. In FIG. 2a, the tip portion 26 includes a plurality of protrusions 21, which have a triangular cross-section, that are positioned on the surface of the catheter, which has a circular cross-section.

Figure 2B:
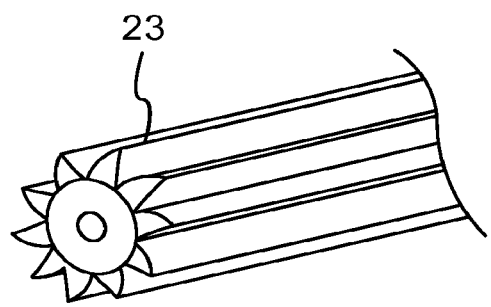
FIG. 2b is angled view of a tip portion of a catheter according to an embodiment of the invention.
Figure 2C:
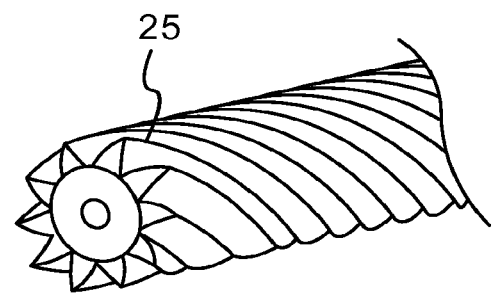
FIG. 2c is angled view of a tip portion of a catheter according to another embodiment of the invention.

According to an embodiment of the invention, protrusions of any size or shape are arranged in a pattern on a surface of the tip portion of the catheter of any cross-sectional shape. For example, the pattern may include one or more continuous ridges on the surface of the tip portion. The ridges may be substantially linear or curved. Examples of catheter tips according to these embodiments are shown in FIGS. 2b and 2c. FIG. 2b shows a tip portion that includes protrusions with triangular cross-section that form a plurality of substantially linear ridges 23 on a catheter with circular cross-section. FIG. 2c shows a tip portion that includes protrusions with triangular cross-section that form a plurality of curved ridges 25 on a catheter with circular cross-section.

Figure 2D:
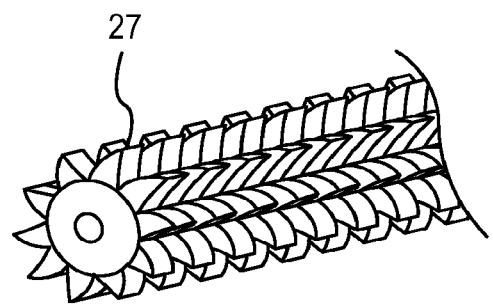
FIG. 2d is angled view of a tip portion of a catheter according to another embodiment of the invention.

According to another embodiment of the invention, the protrusions of any size or shape may be oriented to form one or more discontinuous ridges on a surface of the catheter of any cross-sectional shape. An example of a catheter according to this embodiment is shown in FIG. 2d. FIG. 2d shows a tip portion that includes protrusions with triangular cross-section that form a plurality of discontinuous ridges 27 on a catheter with circular cross-section.

Figure 3A:
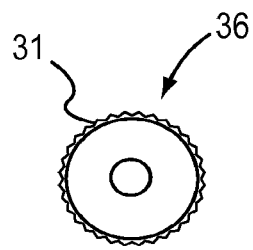
FIG. 3a is a cross-sectional view of a tip portion of a catheter according to another embodiment of the invention.
Figure 3B:
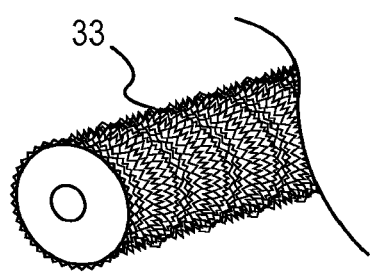
FIG. 3b is angled view of a tip portion of a catheter according to another embodiment of the invention.

According to another embodiment of the invention, one or more protrusions may be of any size or shape and be oriented randomly on a surface of the tip portion of the catheter of any cross-sectional shape. An example of a catheter according to this embodiment is shown in FIGS. 3a and 3b. FIGS. 3a and 3b shows the tip portion 36 of a catheter with a plurality of protrusions 31 that are arranged randomly.

According to another embodiment of the invention, one or more protrusions may be formed integrally with the catheter of any cross-sectional shape. The protrusions may be of any size or shape and may be arranged in any way including, but not limited to, randomly oriented or one or more continuous or discontinuous ridges that are substantially linear or curved.

Figure 4A:
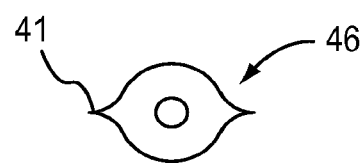
FIG. 4a is a cross-sectional view of a tip portion of a catheter according to another embodiment of the invention.
Figure 4B:
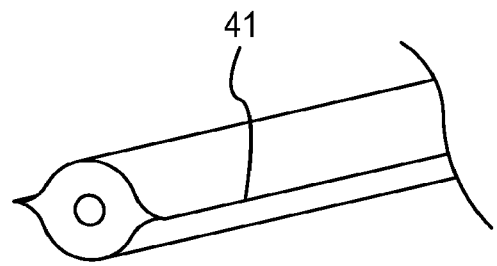
FIG. 4b is angled view of a tip portion of a catheter according to another embodiment of the invention.

An example of a catheter according to this embodiment of the invention is shown in FIGS. 4a and 4b. In FIGS. 4a and 4b, two integrally formed protrusions 41 with triangular cross-section are arranged at opposing sides of the tip portion 46 of the catheter with circular cross-section to form continuous ridges.

The catheter of the present invention may include any combination of the features described above.

Although the catheter of the present invention is described above as being useful for initiating mechanical pleurodesis to treat pleural diseases such as pleural effusions and pneumothorax, the catheter may also be used in any type of medical procedure that requires irritating or roughening a surface. In addition, the catheters may be used in conjunction with other medical instruments including, but not limited to, pleural shunts, ascetic shunts, hydro-cephalic shunts.

What is claimed is:

1. A method of removing fluid and performing mechanical pleurodesis comprising:
   inserting a catheter into a patient's pleural cavity, the catheter comprising a lumen and an outer wall at least partially surrounding the lumen with an external surface extending from a proximal end of the catheter to an opening of the lumen at a distal most tip of the catheter, wherein a distal end portion of the external surface of the catheter comprises a plurality of protrusions thereon;
   using the lumen of the catheter to remove pleural fluid from the patient's pleural cavity; and
   performing mechanical pleurodesis by irritating tissue of the pleural cavity to promote the creation of fibrous adhesions between visceral layers of the pleural cavity, wherein the mechanical pleurodesis is performed by moving the distal end portion of the catheter within the pleural cavity to cause contact between the plurality of protrusions and tissue of the pleural cavity.

2. The method of claim 1, wherein the irritation caused by the plurality of protrusions at the distal end portion causes the creation of fibrous adhesions between a parietal and a visceral layer of the patient's pleura.

3. The method of claim 1, wherein the removed pleural fluid is collected in a drainage container.

4. The method of claim 1, wherein the catheter is formed of a material sufficiently rigid so that the protrusions are able to irritate the tissue of the pleural cavity.

5. The method of claim 4, wherein the material is at least one of a silicone, polyvinyl chloride (PVC), polypropylene, polyurethane, or a thermoplastic elastomer.

6. The method of claim 1, wherein the positioning of the catheter in the patient's body is assisted via use of a cuff that surrounds the outer wall of the catheter.

7. The method of claim 1, wherein tissue that contacts protrusions at the distal end portion closest the distal most tip portion of the catheter is roughened less than tissue that contacts protrusions further from the distal most tip portion of the catheter.

8. The method of claim 7, wherein at least one of a size or shape of the plurality of protrusions are varied along a length of the distal end portion such that larger protrusions are provided at a proximal end thereof and smaller protrusions are present at a distal end closest to the tip portion of the catheter.

9. The method of claim 1, wherein the distal end portion extends from the tip of the catheter.

10. The method of claim 1, wherein the protrusions have a shape selected from a group consisting of circular, elliptical, triangular, rectangular, or other polygonal.

11. A method of performing mechanical pleurodesis comprising:
    inserting a catheter into a patient's pleural cavity, the catheter comprising a lumen and an outer wall at least partially surrounding the lumen with an external surface extending from a proximal end of the catheter to an opening of the lumen at a distal most tip of the catheter, wherein a distal end portion of the external surface of the catheter comprises a plurality of protrusions thereon;
    performing mechanical pleurodesis by irritating tissue of the pleural cavity to promote the creation of fibrous adhesions between visceral layers of the pleural cavity, wherein the mechanical pleurodesis is performed by moving the distal end portion of the catheter within the pleural cavity to cause contact between the plurality of protrusions and tissue of the pleural cavity; and
    using the lumen of the catheter to remove pleural fluid from the patient's plural cavity.

12. The method of claim 11, wherein the removed pleural fluid is collected in a drainage container.

13. The method of claim 11, wherein the irritation caused by the plurality of protrusions at the distal end portion causes the creation of fibrous adhesions between a parietal and a visceral layer of the pleura.

14. The method of claim 11, wherein the catheter is formed of a material sufficiently rigid so that the protrusions are able to irritate the tissue of the pleural cavity.

15. The method of claim 12, wherein the material is at least one of a silicone, polyvinyl chloride (PVC), polypropylene, polyurethane, or a thermoplastic elastomer.

16. An apparatus for removing fluid and performing mechanical pleurodesis between a parietal and a visceral layer of a patient's pleura, the apparatus comprising:
    an elongated tubular member that extends between a proximal end and a distal most tip;
    a lumen; and
    an outer wall at least partially surrounding the lumen with an external surface extending from the proximal end of the tubular member to an opening of the lumen at a distal most tip of the of the tubular member, wherein a distal end portion of the external surface of the tubular member comprises a plurality of protrusions thereon, wherein the tubular member is configured to be inserted into a patient's pleural cavity to remove pleural fluid from the patients pleural cavity via the lumen and the plurality of protrusions at the distal end portion are used to irritate tissue of the pleural cavity to promote the creation of fibrous adhesions between the parietal and a visceral layer of the patient's pleura, wherein the mechanical pleurodesis is performed by moving the distal end portion of the tubular member within the pleural cavity to cause contact between the plurality of protrusions and tissue of the pleural cavity.

17. The apparatus of claim 16, wherein the tubular member is formed of a material sufficiently rigid so that the protrusions are able to irritate the tissue of the pleural cavity.

18. The apparatus of claim 17, wherein the material is at least one of a silicone, polyvinyl chloride (PVC), polypropylene, polyurethane, or a thermoplastic elastomer.

19. The apparatus of claim 16, further comprising a cuff that surrounds the outer wall of the elongated tubular member, wherein the positioning of the elongated tubular member in the patient's body is assisted via use of the cuff.

20. The apparatus of claim 16, wherein at least one of a size or shape of the plurality of protrusions are varied along a length of the distal end portion such that larger protrusions are provided at a proximal end thereof and smaller protrusions are present at a distal end closest to the tip portion of the tubular member.

21. The apparatus of claim 16, wherein the protrusions have a shape selected from a group consisting of circular, elliptical, triangular, rectangular, or other polygonal.

\* \* \* \* \*